(12) United States Patent
Speicher et al.

(10) Patent No.: US 11,304,789 B2
(45) Date of Patent: Apr. 19, 2022

(54) ORAL CAVITY TREATMENT DEVICE AND KIT

(71) Applicant: Colgate-Palmolive Company, New York, NY (US)

(72) Inventors: Erin Speicher, Hoboken, NJ (US); Leighton Davies-Smith, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 248 days.

(21) Appl. No.: 16/593,713

(22) Filed: Oct. 4, 2019

(65) Prior Publication Data

US 2021/0100645 A1    Apr. 8, 2021

(51) Int. Cl.
*A61C 19/06* (2006.01)
*A61N 1/05* (2006.01)

(52) U.S. Cl.
CPC .......... *A61C 19/066* (2013.01); *A61N 1/0548* (2013.01); *A61C 2204/002* (2013.01)

(58) Field of Classification Search
CPC ... A61C 19/066; A61C 19/003; A61C 19/004; A61C 19/06; A61C 19/063; A61C 17/00; A61C 7/00; A61C 7/008; A61C 7/06; A61C 7/36; A61C 17/0211; A61C 17/20; A61N 5/00; A61N 5/0613; A61N 5/06; A61N 2005/0606; A61N 1/0548
USPC ........ 433/32, 37, 29, 5, 6, 18, 19, 215, 216, 433/80, 82, 89; 362/572
See application file for complete search history.

(56) References Cited

U.S. PATENT DOCUMENTS

| | | | |
|---|---|---|---|
| 3,215,139 A | 11/1965 | Dietz | |
| 4,237,574 A | 12/1980 | Kelly et al. | |
| 4,406,658 A | 9/1983 | Lattin et al. | |
| 5,009,617 A * | 4/1991 | Thomas | A61C 19/004 439/239 |
| 5,642,737 A | 7/1997 | Parks | |
| 6,398,713 B1 | 6/2002 | Ewing et al. | |
| 6,893,259 B1 | 5/2005 | Reizenson | |
| 7,156,656 B2 | 1/2007 | Duret | |
| 7,775,795 B2 * | 8/2010 | Khawaled | A61K 8/38 433/32 |
| 8,241,035 B2 | 8/2012 | Jones et al. | |

(Continued)

FOREIGN PATENT DOCUMENTS

| | | |
|---|---|---|
| EP | 1525857 A1 | 4/2005 |
| WO | 2016/051400 | 4/2016 |

*Primary Examiner* — Ralph A Lewis

(57) ABSTRACT

An oral cavity treatment device including a power component and a tray component that are detachably coupled together. The power component may include a housing having a cavity and a power source located therein. The tray component may include a tooth receiving channel and may have a first electrode and a second electrode located on opposite sides of the tooth receiving channel. The tray component may be detachably coupled to the power component in: (1) a first configuration whereby the first electrode is operably coupled to a positive terminal of the power source and the second electrode is operably coupled to a negative terminal of the power source; and (2) a second configuration whereby the first electrode is operably coupled to the negative terminal of the power source and the second electrode is operably coupled to the positive terminal of the power source.

19 Claims, 10 Drawing Sheets

(56) References Cited

U.S. PATENT DOCUMENTS

| | | |
|---|---|---|
| 8,660,669 B2 | 2/2014 | Nemeh et al. |
| 9,730,780 B2 * | 8/2017 | Brawn ..................... A61C 7/08 |
| 9,839,500 B2 * | 12/2017 | Flyash ................. A61C 19/066 |
| 2001/0012608 A1 | 8/2001 | Darnell |
| 2005/0202363 A1 | 9/2005 | Osterwalder |
| 2007/0015112 A1 | 1/2007 | Hochman et al. |
| 2008/0233541 A1 | 9/2008 | De Vreese et al. |
| 2009/0029311 A1 | 1/2009 | Chan |
| 2009/0117513 A1 | 5/2009 | Nemeh et al. |
| 2013/0045457 A1 | 2/2013 | Chetiar et al. |
| 2013/0209964 A1 * | 8/2013 | Nemeh .................. A61C 19/06 433/216 |
| 2013/0280671 A1 * | 10/2013 | Brawn ................ A61N 5/0603 433/24 |
| 2014/0023983 A1 * | 1/2014 | Lowe ...................... A61C 7/08 433/24 |
| 2015/0044628 A1 | 2/2015 | Flyash |
| 2017/0173353 A1 * | 6/2017 | Demarest ............ A61C 19/063 |
| 2017/0360973 A1 * | 12/2017 | Saue .................... H02M 3/335 |
| 2018/0078339 A1 * | 3/2018 | Johnson ................ A61C 17/20 |
| 2018/0125627 A1 * | 5/2018 | Mounce ................ A61Q 11/00 |
| 2018/0344440 A1 * | 12/2018 | Dorward ............. A61C 17/022 |
| 2019/0000601 A1 * | 1/2019 | Huang ................ A46B 13/023 |
| 2019/0159877 A1 * | 5/2019 | Sanders ............... A61C 19/066 |

* cited by examiner

ORAL CAVITY TREATMENT DEVICE AND KIT

BACKGROUND

Tray based oral cavity treatment systems have been developed to whiten teeth and complete other treatments in the oral cavity that can be completed at home or in a doctor's office. For example, some of these trays emit electromagnetic radiation and/or a current into a tooth receiving channel of the tray to enhance a treatment being performed with a particular oral composition. However, a consumer must typically purchase a different tray system for each treatment desired, which can become expensive. Thus, a need exists for a tray-based treatment system that enables different treatments to be performed with one device.

BRIEF SUMMARY

In one aspect, the invention may be an oral cavity treatment device comprising: a power component comprising a housing having a cavity and a power source located in the cavity; a tray component comprising a tooth receiving channel, a first electrode operably coupled to a first electrical contact, and a second electrode operably coupled to a second electrical contact, the first and second electrodes being located on opposite sides of the tooth receiving channel; and wherein the tray component is detachably coupled to the power component in: (1) a first configuration whereby the first electrical contact is operably coupled to a positive terminal of the power source and the second electrical contact is operably coupled to a negative terminal of the power source; and (2) a second configuration whereby the first electrical contact is operably coupled to the negative terminal of the power source and the second electrical contact is operably coupled to the positive terminal of the power source.

In another aspect, the invention may be an oral cavity treatment device comprising: a tray component comprising a first electrode and a second electrode located on opposite sides of a tooth receiving channel, a first connection member comprising a first mechanical connector and a first electrical contact that is operably coupled to the first electrode, and a second connection member comprising a second mechanical connector and a second electrical contact that is operably coupled to the second electrode; a power component comprising a cavity that houses a power source, a third connection member comprising a third mechanical connector and a third electrical contact that is operably coupled to a positive terminal of the power source, and a fourth connection member comprising a third mechanical connector and a fourth electrical contact that is operably coupled to a negative terminal of the power source; wherein the tray component and the power component are detachably coupled together and can be altered between: (1) a first attached configuration whereby: (a) the first and third connection members mate so that the first and third mechanical connectors are coupled together and the first and third electrical contacts are in contact to couple the first electrode to the positive terminal of the power source; and (b) the second and fourth connection members mate so that the second and fourth mechanical connectors are coupled together and the second and fourth electrical contacts are in contact to couple the second electrode to the negative terminal of the power source; (2) a second attached configuration whereby: (a) the first and fourth connection members mate so that the first and fourth mechanical connectors are coupled together and the first and fourth electrical contacts are in contact to couple the first electrode to the negative terminal of the power source; and (b) the second and third connection members mate so that the second and third mechanical connectors are coupled together and the second and third electrical contacts are in contact to couple the second electrode to the positive terminal of the power source; and (3) a detached configuration whereby the tray component and the power component are separated from one another.

In yet another aspect, the invention may be an oral cavity treatment kit comprising: a power component comprising a housing having a cavity and a power source located in the cavity, the power source comprising a positive terminal and a negative terminal; a first tray component comprising a tooth receiving channel defined between inner and outer sidewalls, a first electrode located along the inner sidewall, and a second electrode located along the outer sidewall; and a second tray component comprising a tooth receiving channel defined between inner and outer sidewalls, a first electrode located along the inner sidewall, and a second electrode located along the outer sidewall; wherein at least one of: the first electrode of the first tray component is formed from a different material than the first electrode of the second tray component; and the second electrode of the second tray component is formed from a different material than the second electrode of the second tray component; wherein the first tray component is detachably coupled to the power component so that the first electrode is operably coupled to one of the positive and negative terminals of the power source and the second electrode is operably coupled to the other one of the positive and negative terminals of the power source; and wherein the second tray component is detachably coupled to the power component so that the first electrode is operably coupled to one of the positive and negative terminals of the power source and the second electrode is operably coupled to the other one of the positive and negative terminals of the power source.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
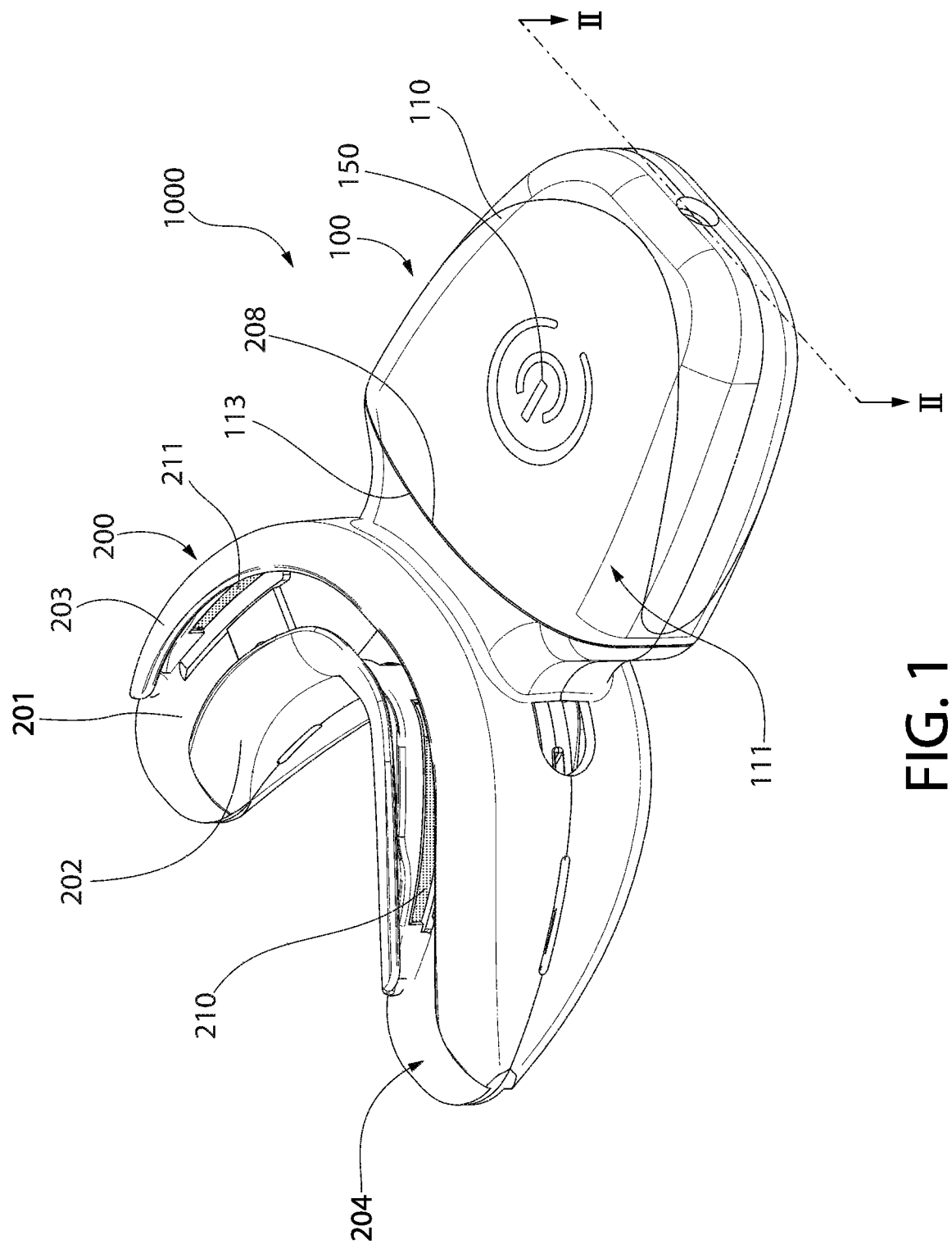
FIG. 1 is a perspective view of an oral cavity treatment device having a tray component and a power component in a first assembled configuration.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

In an embodiment, the present invention may be directed to a modular, powered tray that is sectioned into two removable components (a power component and a tray component), so that different tray components can be coupled to a common power component, in different orientations, for different oral care applications. The tray component that is inserted into the user's mouth contains electrodes of various metal materials depending on the target benefit. For example, a tray with titanium electrodes for whitening applications, a tray with one or more zinc electrodes for anti-bacterial, etc. The electrodes are positioned on either side of the teeth surfaces during a treatment. For each oral care application, the polarity of the electrodes is important because it drives the direction of the chemical reaction, which may be different for different oral care indications. For instance, it is desirable to have whitening occur on the outer surfaces of the teeth, but when targeting anti-bacterial reduction, it is desirable to target the back of the teeth since more bacteria is located near the tongue. Thus, a tray with titanium electrodes may need polarity in one direction whereas a tray with zinc electrodes may need polarity in another direction.

The power component described in some embodiments of this invention may include two ports, one positive and one negative, that will make electronic connection with the electrode connectors that are part of the tray component (although the ports could be in the tray component and the power component could have the electrode connectors in other embodiments). The tray component can be connected to the power component in either orientation, depending on the indication being targeted by the user, and this orientation will drive the polarity of the electrodes, and thus the direction of the reaction. One benefit of this invention is that one power component contains the battery (rechargeable or not) and electronic components of the device, which can be used with multiple tray components, depending on the benefit that the user is looking to receive. Additionally, since some oral care indications would require changing the polarity of the electrodes, this can be controlled at the point of user interaction, as opposed to software changes which would be required if the tray component was one single component. This invention makes treating different oral care problems easier with one power component and different tray components, but it also reduces manufacturing complexity since mouth trays can be all be made to the same design, using different electrode materials.

Figure 2:
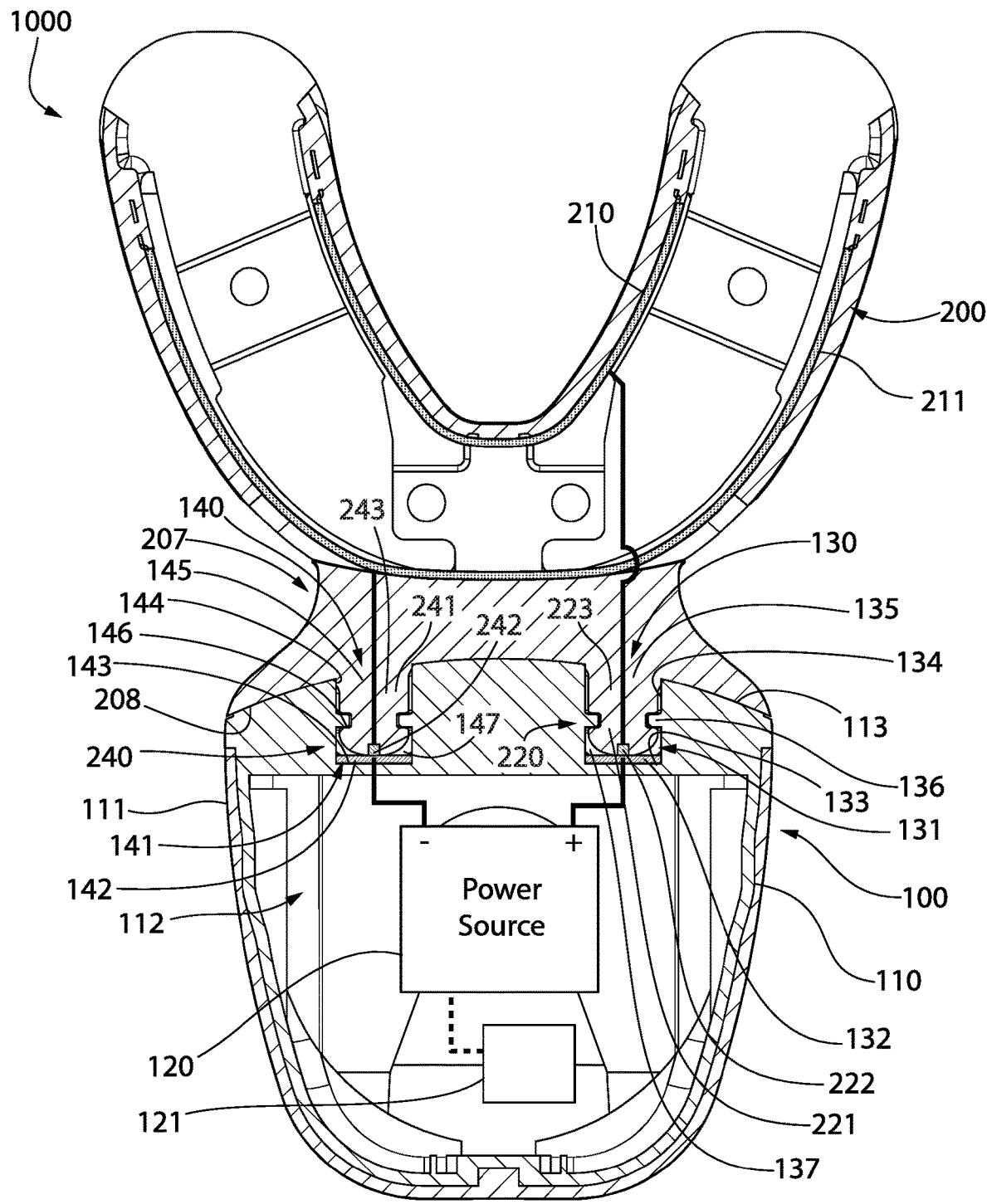
FIG. 2 is a cross-sectional view taken along line II-II of FIG. 1.
Figure 3:
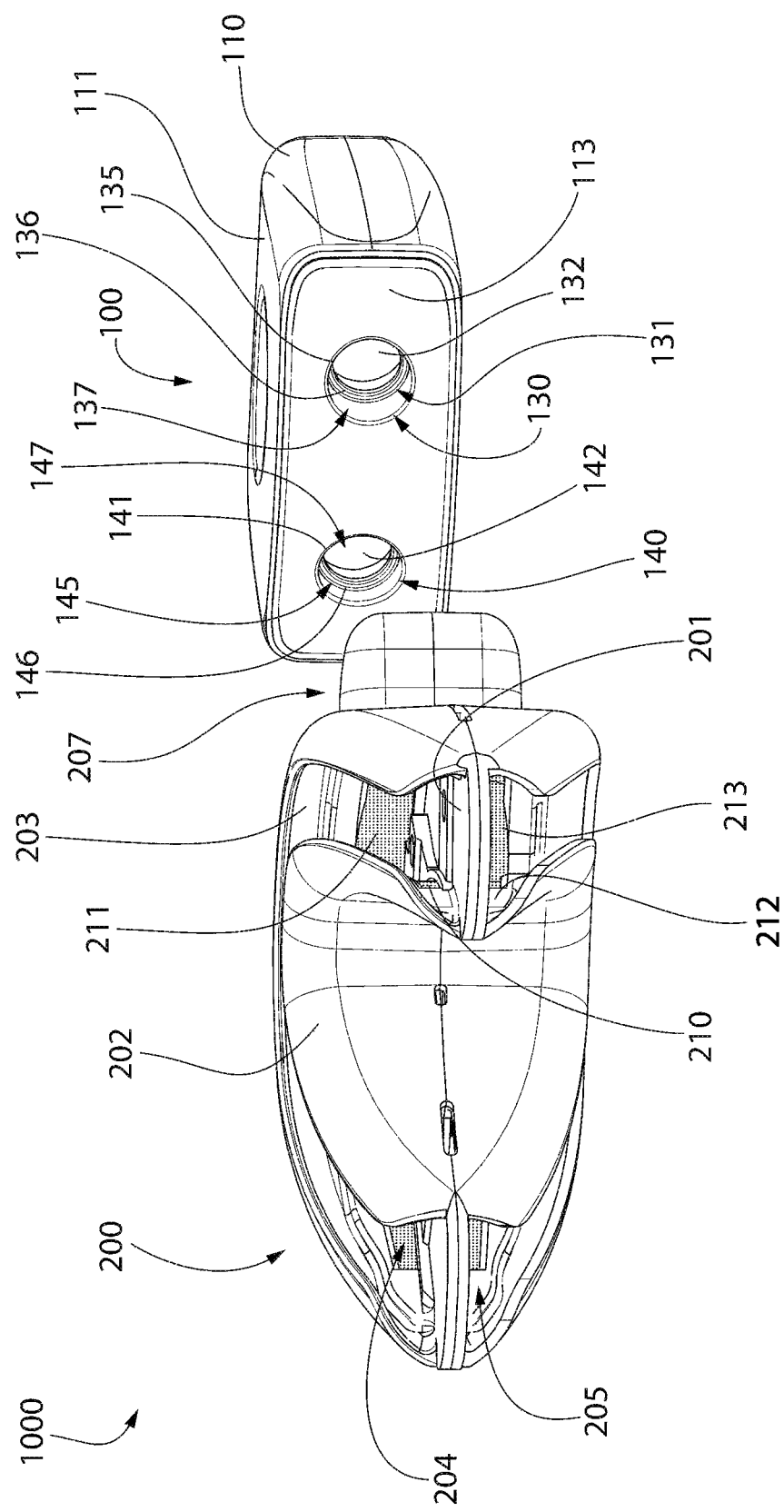
FIG. 3 is a front perspective view of the oral cavity treatment device of FIG. 1 in a disassembled configuration.

Referring to FIGS. 1-3 concurrently, an oral cavity treatment device 1000 will be described in accordance with an embodiment of the present invention. The oral cavity treatment device 1000 generally comprises a power component 100 and a tray component 200. The power component 100 and the tray component 200 are detachably coupled together, and they are illustrated in a first assembled configuration in FIG. 1 and in a disassembled configuration in FIG. 3. The power component 100 may form a sort of handle for the oral cavity treatment device 1000 and the tray component 200 may be the portion of the oral cavity treatment device 1000 that is placed into the user's oral cavity to perform a treatment. The details of the manner of attaching/detaching the power component 100 and the tray component 200 from one another will be described in greater detail below.

The power component 100 comprises a housing 110 having an outer surface 111. Furthermore, the housing 110 has or defines a cavity 112 within which one or more electric components may be located. In the exemplified embodiment, the power component 100 comprises a power source 120 and an electronic circuit 121 that is operably coupled to the power source. In some embodiments, the electronic circuit 121 may comprise one or more of a controller/processer, a memory, indicators such as light emitting diodes, switches, timers, and the like. Moreover, it should be appreciated that the electronic circuit 121 could be omitted in some embodiments because in the broadest sense all that may be required for operation of the oral cavity treatment device 1000 is the power source and the electric components of the tray component 200 described below.

The outer surface 111 of the housing 110 comprises a first engagement surface 113, which is the portion of the outer surface 111 of the housing 110 that contacts/engages the tray component 200 when the power component 100 is coupled to the tray component 200. In the exemplified embodiment, the first engagement surface 113 has a concave shape. However, the invention is not to be so limited in all embodiments and the first engagement surface 113 could be planar/flat/straight, convex, wavy, or the like in other embodiments so long as it is configured to mate with an engagement surface of the tray component 200 as described below. Also, it should be noted that the specific shape of the housing 110 is not limiting of the invention described herein. The power component 100 remains outside of the user's oral cavity at all times, so it does not need to have a particular shape to interact with parts of the oral cavity. Rather, the power component 100 merely contains the electronic components (i.e., the power source 120 and any other electronic components such as those that are part of the electronic circuit 121) to facilitate powering electrodes of the tray component 200.

The power component 100 comprises a third connection member 130 and a fourth connection member 140 that facilitate both mechanically and electrically coupling the power component 100 to the tray component 200. The third connection member 130 comprises a third mechanical connector 131 and a third electrical contact 132. The fourth connection member 140 comprises a fourth mechanical connector 141 and a fourth electrical contact 142. In the exemplified embodiment, the third mechanical connector 131 is a cavity or recess 137 and the fourth mechanical connectors 131, 141 is a cavity or recess 147 formed into the first engagement surface 113 of the housing 110. However, the invention is not to be so limited in all embodiments. Rather, in other embodiments the third and fourth mechanical connectors 131, 141 could be protuberances, screw threads, straps, hooks, fasteners, bolts, plates, combinations thereof, or the like. Basically, the third and fourth mechanical connectors 131, 141 can take on any structural configuration so long as they are configured to mate with mechanical connectors of the tray component 200 to facilitate coupling the power component 100 to the tray component 200.

As noted above, in the exemplified embodiment the third and fourth mechanical connectors 131, 141 are cavities 137, 147. In that regard, the third mechanical connector 131 comprises a floor 133 and a sidewall 134 extending from the floor 133 to an opening 135 in the first engagement surface 113 of the housing 111. In the exemplified embodiment, the cavity 137 of the third mechanical connector 131 comprises a locking feature 136. In the exemplified embodiment, the locking feature 136 is a locking protuberance extending from the sidewall 134 to facilitate locking of the tray component 200 to the power component 100. The locking protuberance is an annular feature in the exemplified embodiment, but need not be in all embodiments. Thus, the locking protuberance could be formed by multiple spaced apart protuberances in some embodiments. Further still, the locking feature 136 could be a locking recess in other embodiments so long as it is configured to interact with a locking feature of the tray component 200 as described herein below.

Similarly, the fourth mechanical connector 141 comprises a floor 143 and a sidewall 144 extending from the floor 143 to an opening 145 in the first engagement surface 113 of the housing 111. In the exemplified embodiment, the cavity 147 of the fourth mechanical connector 141 comprises a locking feature 146. In the exemplified embodiment, the locking feature 146 comprises a locking protuberance extending from the sidewall 144 to facilitate locking of the tray component 200 to the power component 100. The locking protuberance is an annular feature in the exemplified embodiment, but need not be in all embodiments. Thus, the locking protuberance could be formed by multiple spaced apart protuberances in some embodiments. Further still, the locking feature 146 could be a locking recess in other embodiments so long as it is configured to interact with a locking feature of the tram component 200 as described herein below.

In the exemplified embodiment the third electrical contact 132 is located within the cavity 137 that forms the third mechanical connector 131. More specifically, in the exemplified embodiment the third electrical contact 132 is located on the floor 133 of the third mechanical connector 131. However, the invention is not to be so limited in all embodiments and the third electrical contact 132 could be located on the sidewall 134 in other embodiments. Moreover, in the exemplified embodiment the third electrical contact 132 is depicted as a flat plate-like member. However, the third electrical contact 132 can take on other structural configurations, including extending vertically like a pin from the floor 133 to promote engagement with electrical contacts of the tray component 200 as described in more detail below.

The third electrical contact 132 is operably coupled to a positive terminal of the power source 120. In the exemplified embodiment, this is illustrated as being achieved by a conductive wire being coupled to the positive terminal of the power source 120 and to the third electrical contact 132. The third electrical contact 132 is formed of an electrically conductive material such as a metal and it functions basically as the positive terminal of the power source 120 due to its coupling thereto.

In the exemplified embodiment, the fourth electrical contact 142 is located within the cavity 147 that forms the fourth mechanical connector 141. More specifically, in the exemplified embodiment the fourth electrical contact 142 is located on the floor 143 of the fourth mechanical connector 141. However, the invention is not to be so limited in all embodiments and the fourth electrical connector 142 could be located on the sidewall 144 in other embodiments. Moreover, in the exemplified embodiment the fourth electrical contact 142 is depicted as a flat plate-like member. However, the fourth electrical contact 142 can take on other structural configurations, including extending vertically like a pin from the floor 143 to promote engagement with electrical contacts of the tray component 200 as described in more detail below.

The fourth electrical contact 142 is operably coupled to a negative terminal of the power source 120. In the exemplified embodiment, this is illustrated as being achieved by a conductive wire being coupled to the negative terminal of the power source 120 and to the fourth electrical contact 142. The fourth electrical contact 142 is formed of an electrically conductive material such as a metal and it functions basically as the negative terminal of the power source 120 due to its coupling thereto.

In the exemplified embodiment, the power component 100 comprises an actuator 150 located on the outer surface 111 of the housing 110. In the exemplified embodiment, the actuator 150 is a depressible button, but it could be a slide switch, a conductive switch, or any other type of mechanism as may be desired. The actuator 150 is operably coupled to the power source 120 so that actuation of the actuator 150 causes the power source 120 to transmit power to the tray component 200 (and specifically to electrodes thereof as described herein below) when the tray component 200 is coupled to the power component 100 as described herein below.

The tray component 200 is the part of the oral cavity treatment device 1000 that is intended to be placed inside of a user's mouth during a treatment. Thus, the tray component 200 is preferably formed, at least in part, of a malleable or flexible or rubber-like material to enhance comfort when worn by a user. However, the invention is not to be so limited and the tray component 200 may be formed of rigid materials such as plastic, metal, or the like in other embodiments. In some embodiments the tray component 200 may include a rigid core and a soft or flexible covering over a part of or the entirety of the rigid core, the covering being formed of a rubber-like material such as a thermoplastic elastomer or the like.

The tray component 200 comprises a floor 201 which forms a biting surface of the tray component 200, an inner sidewall 202 extending from the floor 201, and an outer sidewall 203 extending from the floor 201. The inner and outer sidewalls 202 are spaced apart from one another by the floor 202 such that the inner and outer sidewalls 202 extend from opposing ends of the floor. The floor 201, the inner sidewall 202, and the outer sidewall 203 collectively form a tooth receiving channel 204 of the tray component 200 within which a user's teeth are positioned during a treatment.

In the exemplified embodiment, the inner and outer sidewalls 202, 203 extend both upwardly from the floor 201 and downwardly from the floor 201, perhaps best seen in FIG. 3. Thus, in the exemplified embodiment the tray component 200 comprises an upper tooth receiving channel (which is the tooth receiving channel 204) and a lower tooth receiving channel 205. This enables the tray component 200 to be positioned within the oral cavity with the user's upper teeth located within the upper tooth receiving channel 204 and the user's lower teeth simultaneously located within the lower tooth receiving channel 205 (or vice versa). However, the invention is not to be so limited in all embodiments. In some embodiments, the tray component 200 may include only one of the tooth receiving channels 204, 205 such that the inner and outer sidewalls 202, 203 may extend in only one direction from the floor 201.

The tray component 200 comprises a first electrode 210 positioned along the inner sidewall 202 and a second electrode 211 positioned along the outer sidewall 203 along the upper tooth receiving channel 204. The tray component 200 also comprises a first electrode 212 positioned along the inner sidewall 202 and a second electrode 213 positioned along the outer sidewall 203 along the lower tooth receiving channel 204. Thus, the first and second electrodes 210, 211 are located on opposite sides of the upper tooth receiving channel 204 and the first and second electrodes 212, 213 are located on opposite sides of the lower tooth receiving channel 205. As mentioned above, the lower tooth receiving channel 205 may be omitted in some embodiments.

The first and second electrodes 210, 211, 212, 213 may be formed of any of a number of different materials depending on their end use. For example, if the first and second electrodes 210, 211, 212, 213 are going to be used for a tooth whitening treatment, they may be formed from titanium whereas if the first and second electrodes 210, 211, 212, 213 are going to be used for an antibacterial treatment, they may be formed from zinc. In the exemplified embodiment, portions of the first and second electrodes 210, 211, 212, 213 are illustrated being exposed to the tooth receiving channels 204, 205. However, the invention is not to be so limited in all embodiments and in other embodiments the first and second electrodes 210, 211, 212, 213 may be embedded within one of the inner and outer sidewalls 202, 203.

Although titanium and zinc are two potential materials for the electrodes, in other embodiments other materials may be used depending on the desired treatment. The table provided below indicates some additional electrode materials that can be used along with the oral care composition that can be used with those electrodes and the indication or treatment being performed. It should be noted that in the table provided below platinum could be substituted for platinized titanium (PtTi) for all the indications.

| Indication | Electrode Materials/Solution | | |
|---|---|---|---|
| Whitening | ⊕ PtTi | Hydrogen Peroxide | ⊖ PtTi |
| Whitening | ⊕ Steel | $Fe^{2+}$ & HP | ⊖ PtTi |
| Sensitivity | ⊕ PtTi | $K^+$ | ⊖ PtTi |
| Anti caries | ⊕ PtTi | $F^-$ | ⊖ PtTi |
| Gingivitis | ⊕ PtTi | $Zn^{2+}$ | ⊖ PtTi or Zn |
| Antibacterial | ⊕ PtTi | $Zn^{2+}$ | ⊖ PtTi or Zn |

In some embodiments, the material of the first and second electrodes 210, 211 on the opposing sides of the upper tooth receiving channel 204 may be different than the material of the first and second electrodes 212, 213 on the opposing sides of the lower tooth receiving channel 205. Thus, for example, the first and second electrodes 210, 211 may be formed from titanium and used for whitening and the first and second electrodes 212, 213 may be formed from zinc and used for antibacterial treatment. Thus, a different polarity may be desired for the first and second electrodes 210, 211 as compared to the first and second electrodes 212, 213, and this can be achieved with the present invention described herein.

Referring to FIGS. 1-4, a surface of the outer sidewall 203 of the tray component 200 that faces away from the tooth receiving channels 204, 205 forms a rear surface 206 of the tray component 200. Furthermore, the tray component 200 comprises a connection feature 207 protruding from the rear surface 206 of the tray component 200. A terminal end of the connection feature 207 forms a second engagement surface 208 of the tray component 200. The second engagement surface 208 of the tray component 200 is configured to abut, mate, or otherwise interact with the first engagement surface 113 of the power component 100 when the tray component 200 is coupled to the power component 100. In that regard, in the exemplified embodiment the second engagement surface 208 is concave to mate with the convex shape of the first engagement surface 113 of the power component 100. However, the shape of the second engagement surface 208 may be changed to match or correspond to the shape of the first engagement surface 113.

The tray component 200 further comprises a first connection member 220 and a second connection member 240. The first and second connection members 220, 240 are configured to mate with the third and fourth connection members 130, 140 of the power component 100 to facilitate both mechanically and electrically coupling the tray component 200 to the power component 100. In that regard, the first connection member 220 comprises a first mechanical connector 221 and a first electrical contact 222 and the second connection member 240 comprises a second mechanical connector 241 and a second electrical contact 242. The first electrical contact 222 is operably coupled to the first electrode 210 and the second electrical contact 242 is operably coupled to the second electrode 211. In the exemplified embodiment, this is achieved with a conductive wire although other techniques can be used including having the first and second electrical contacts 222, 242 extend directly from the first and second electrodes, 210, 211, or the like.

As will be described further below, the first mechanical connector 221 of the tray component 200 mates with one of the third and fourth mechanical connectors 131, 141 of the power component 100 and the second mechanical connector 241 of the tray component 200 mates with the other one of the third and fourth mechanical connectors 131, 141 of the power component 100 to physically or mechanically couple the tray component 200 to the power component 100. Furthermore, as the first and second mechanical connectors 221, 241 of the tray component 200 mate with the third and fourth mechanical connectors 131, 141 of the power component 100, the first and second electrical contacts 222, 242 of the tray component 200 come into contact with the third and fourth electrical contacts 132, 142 of the power component 100. Because the third and fourth electrical contacts 132, 142 of the power component 100 are operably coupled to the power source 120 and the first and second electrical contacts 222, 242 of the tray component 200 are operably coupled to the first and second electrodes 210, 211, this also puts the first and second electrodes 210, 211 into operable coupling with the power source 120.

In the exemplified embodiment, the first mechanical connector 221 comprises a first protuberance 223 that protrudes from the second engagement surface 208 of the tray component 200. Similarly, the second mechanical connector 241 comprises a second protuberance 243 that protrudes from the second engagement surface 208 of the tray component 200. Furthermore, in the exemplified embodiment the first electrical contact 222 is located on the first protuberance 223 and the second electrical contact 242 is located on the second protuberance 243. More specifically, the first electrical contact 222 is exposed at a distal end 224 of the first protuberance 223 and the second electrical contact 242 is exposed at a distal end 244 of the second protuberance 243. In the exemplified embodiment, an outer surface of the first electrical contact 222 is flush with the distal end 224 of the first protuberance 223 and an outer surface of the second electrical contact 242 is flush with the distal end 244 of the second protuberance 243. However, the first and second electrical contacts 222, 242 could be recessed relative to the distal ends 224, 244 of the first and second protuberances 223, 243 in other embodiments. The exact location and positioning of the first and second electrical contacts 222, 242 along the protuberances 223, 243 is not to be limiting of the present invention as long as the first and second electrical contacts 222, 242 of the tray component 200 come into contact with the third and fourth electrical contacts 122, 132 of the power component 100 when the tray component 200 is coupled to the power component 100

In the exemplified embodiment, the first protuberance 223 comprises a locking feature 225 formed thereon and the second protuberance 243 comprises a locking feature 245 formed therein. In the exemplified embodiment, the locking features 225, 245 are recesses. Thus, the locking features 225, 245 are configured to mate with the locking features 136, 146 of the power component 100 to facilitate maintaining the power component 100 and the tray component 200 in an attached state when so desired. Although in the exemplified embodiment the locking features 225, 245 of the first and second mechanical connectors 221, 241 of the tray component 200 are recesses and the locking features 136, 146 of the third and fourth mechanical connectors 131, 141 of the power component 100 are protuberances, this could be reversed in other embodiments (i.e., the locking protuberances could be formed on the first and second mechanical connectors 221, 241 of the tray component 200 and the locking recesses could be formed on the third and fourth mechanical connectors 131, 141 of the power component 100).

Other structural configurations are also possible to lock the first and second mechanical connectors 221, 241 of the tray component 200 to the third and fourth mechanical connectors 131, 141 of the power component 100. In some embodiments, the locking features 136, 146, 225, 245 may be omitted and the coupling between the tray component 200 and the power component 100 may be achieved by an interference or friction-type fit between the first and second mechanical connectors 221, 241 with the third and fourth mechanical connectors 131, 141.

Moreover, although in the exemplified embodiment the first and second mechanical connectors 221, 241 of the tray component 200 comprise protuberances (i.e., the first and second protuberances 223, 243) and the third and fourth mechanical connectors 131, 141 of the power component 100 comprise the cavity or recess 137, 147, in other embodiments this could be reversed. Thus, the first and second mechanical connectors 221, 241 of the tray component 200 could comprise cavities or recesses while the third and fourth mechanical connectors 131, 141 of the power component 100 comprise protuberances that mate with the cavities or recesses. In still other embodiments, the first, second, third, and fourth mechanical connectors 221, 241, 131, 141 may comprise interlocking features that couple together through a sliding action, and they need not comprise mating protuberances and cavities/recesses in all embodiments. The first, second, third, and fourth mechanical connectors 221, 241, 131, 141 may comprise hooking elements, adhesive, hook-and-loop, bolts and mating openings, mating screw threads, or the like. Moreover, in the exemplified embodiment whereby the first, second, third, and fourth mechanical connectors 221, 241, 131, 141 are protuberances and cavities, they are shown as having a circular cross-sectional shape. However, the invention is not to be so limited and this shape could be polygonal so long as they correspond with one another to facilitate the coupling.

In FIGS. 1 and 2, the oral cavity treatment device 1000 is depicted in a first attached configuration whereby the tray component 200 is coupled to the power component 100. In this arrangement/configuration, the first connection member 220 of the tray component 200 mates with third connection member 130 of the power component 100 while the second connection member 240 of the tray component 200 simultaneously mates with the fourth connection member 140 of the power component 100. Specifically, the first mechanical connector 221 of the tray component 200 mechanically mates with the third mechanical connector 131 of the power component 100. And more specifically, in this embodiment the protuberance 223 of the first mechanical connector 221 of the tray component 200 is disposed within the cavity/recess 137 of the third mechanical connector 131 of the power component 100. Similarly, the second mechanical connector 241 of the tray component 200 mechanically mates with the fourth mechanical connector 141 of the power component 100. And more specifically, in this embodiment the protuberance 243 of the second connection member 241 of the tray component 200 is disposed within the cavity/recess 147 of the fourth mechanical connector 141 of the power component 100.

When the first and third mechanical connectors 221, 131 and the second and fourth mechanical connectors 241, 141 are physically/mechanically coupled together in this way, there is also a coupling among/between the electrical contacts. Specifically, as shown in FIG. 2, coupling the first and third mechanical connectors 221, 131 together also causes the first electrical contact 222 of the tray component 200 to come into contact with the third electrical contact 132 of the power component 100. Moreover, because the first electrical contact 222 is operably coupled to the first electrode 210 and the third electrical contact 132 is operably coupled to the positive terminal of the power source 120, this contact between the first and third electrical contacts 222, 132 operably couples the first electrode 210 to the positive terminal of the power source 120.

Furthermore, coupling the second and fourth mechanical connectors 241, 141 together also causes the second electrical contact 242 of the tray component 200 to come into contact with the fourth electrical contact 142 of the power component 100. Specifically, as shown in FIG. 2, coupling the second and fourth mechanical connectors 241, 141 together also causes the second electrical contact 242 of the tray component 200 to come into contact with the fourth electrical contact 142 of the power component 100. Moreover, because the second electrical contact 242 is operably coupled to the second electrode 211 and the fourth electrical contact 142 is operably coupled to the negative terminal of the power source 120, this contact between the second and fourth electrical contacts 242, 142 operably couples the second electrode 211 to the negative terminal of the power source 120.

As noted above, the oral cavity treatment device 1000 is configured to be modular. In accordance with this invention, this means that the tray component 200 can also be coupled to the power component 100 via engagement between the first and fourth connection members 220, 130 and engagement between the second and third connection members 240, 140. Such modification to the coupling will result in a change/reversal of the polarity of the first and second electrodes 210, 211. Specifically, when the tray component 200 is coupled to the power component 100 in the manner described above, the first electrode 210 is coupled to the positive terminal of the power source 120 and the second electrode 211 is coupled to the negative terminal of the power source 120. When the first and fourth connection members 220, 130 are coupled and the second and third connection members 240, 140 are coupled, the first electrode 210 is coupled to the negative terminal of the power source 120 and the second electrode 211 is coupled to the positive terminal of the power source 120. Thus, depending on the treatment being performed and the polarity of the electrodes 210, 211 needed for that treatment, a user can simply flip one of the tray component 200 and the housing component 100 relative to the other and reconnect them in a second assembled configuration very easily.

Figure 4:
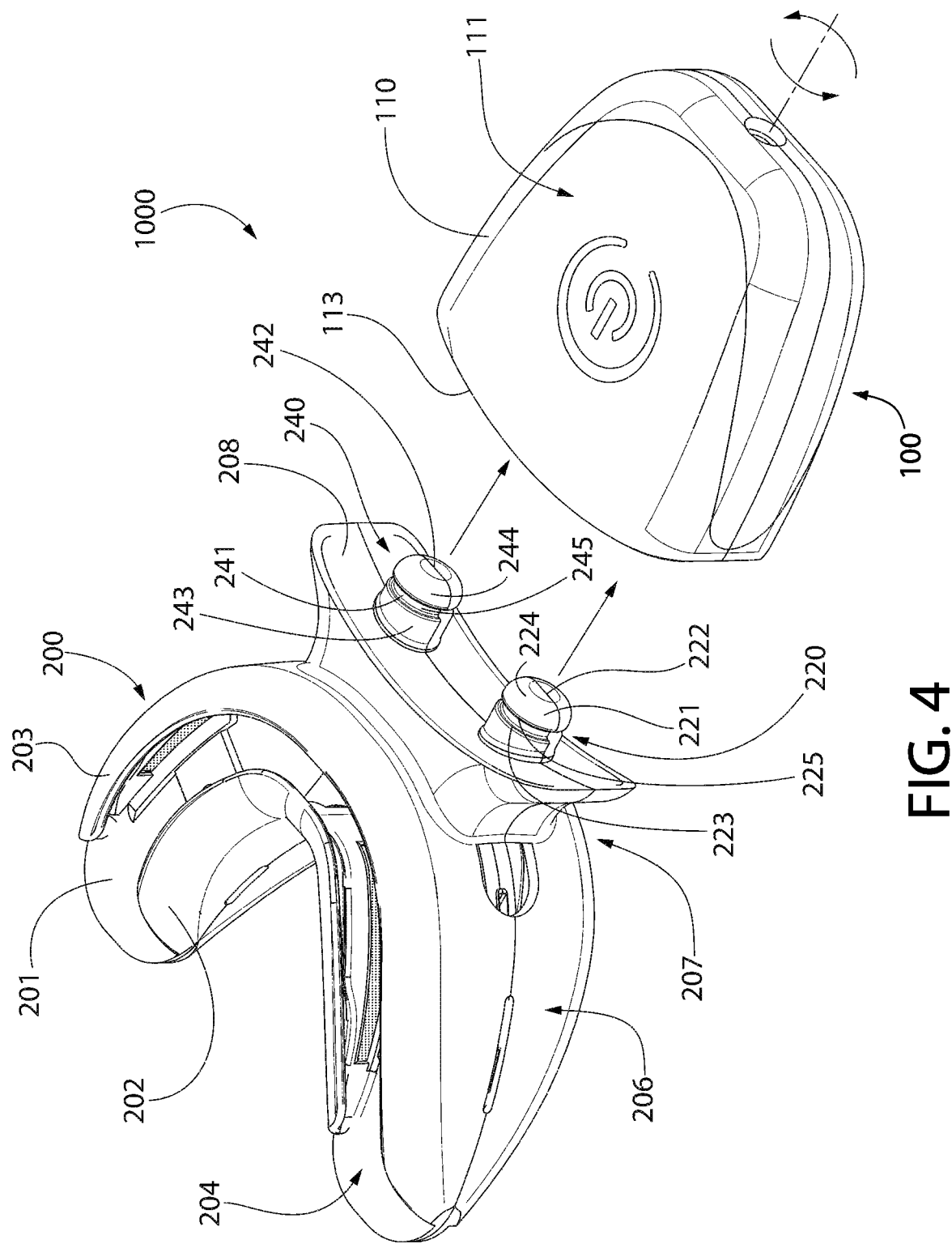
FIG. 4 is a rear perspective view of the oral cavity treatment device of FIG. 1 in a disassembled configuration.
Figure 6:
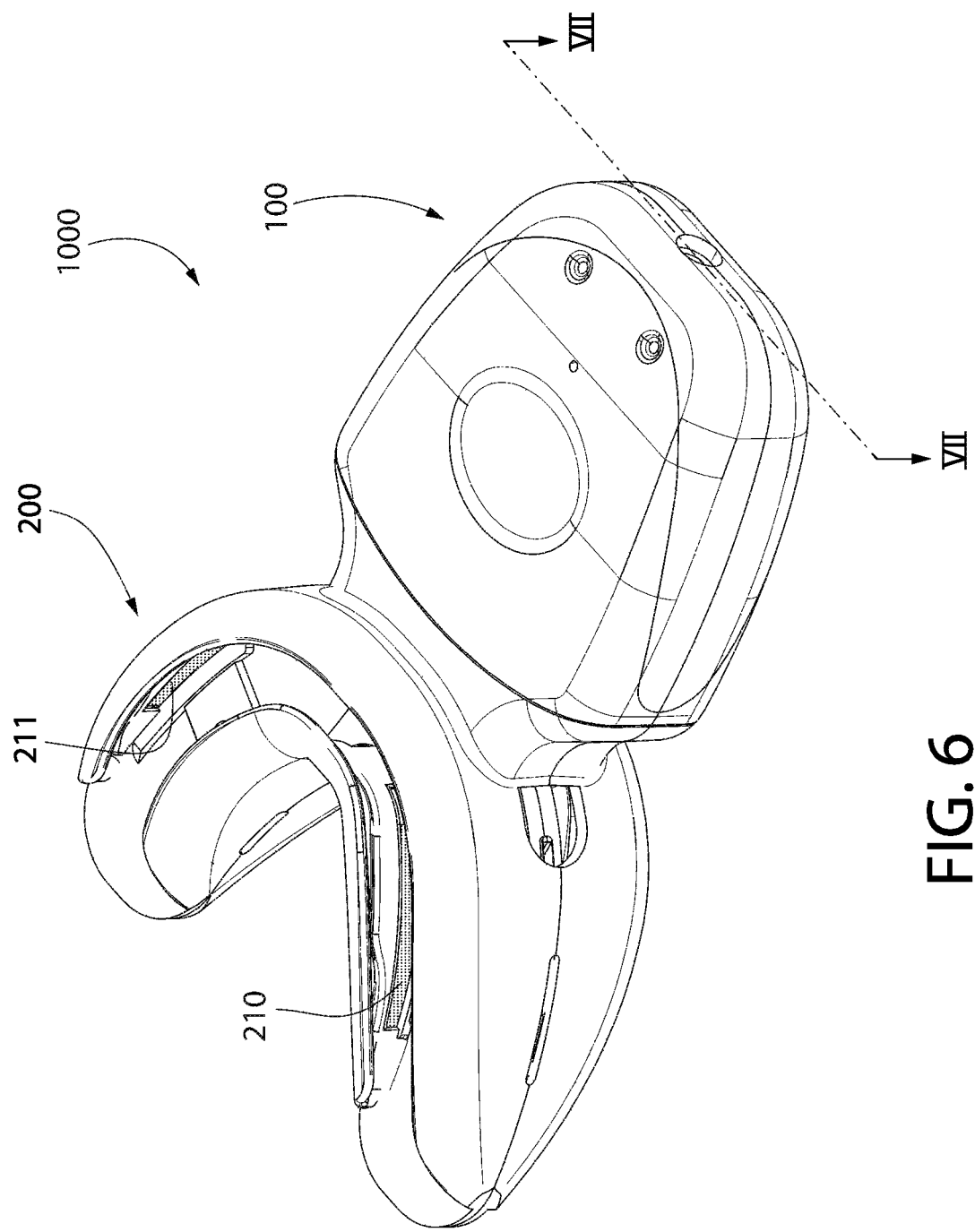
FIG. 6 is a perspective view of the oral cavity treatment device of FIG. 1 in a second assembled configuration.

In that regard, referring first to FIG. 4, the oral cavity treatment device 1000 can be altered from the first assembled configuration (FIG. 1) to a second assembled configuration (FIG. 6). The first step in this process is to detach the tray component 200 from the power component 100, which is what is shown in FIG. 4. As the arrows indicate, the power component 100 is merely pulled away from the tray component 200 with sufficient force to separate the first and second mechanical connectors 221, 241 from the third and fourth mechanical connectors 131, 141 to detach the power component 100 from the tray component 200. Next, either the tray component 200 is rotated 180° relative to the power component 100 or the power component 100 is rotated 180° relative to the tray component 200. In FIG. 4, the rotation arrows are indicated as being related to the power component 100 such that the power component 100 is the one rotating, but the invention does not require this and either the tray component 200 or the power component 100 can be rotated relative to the other.

Figure 5:
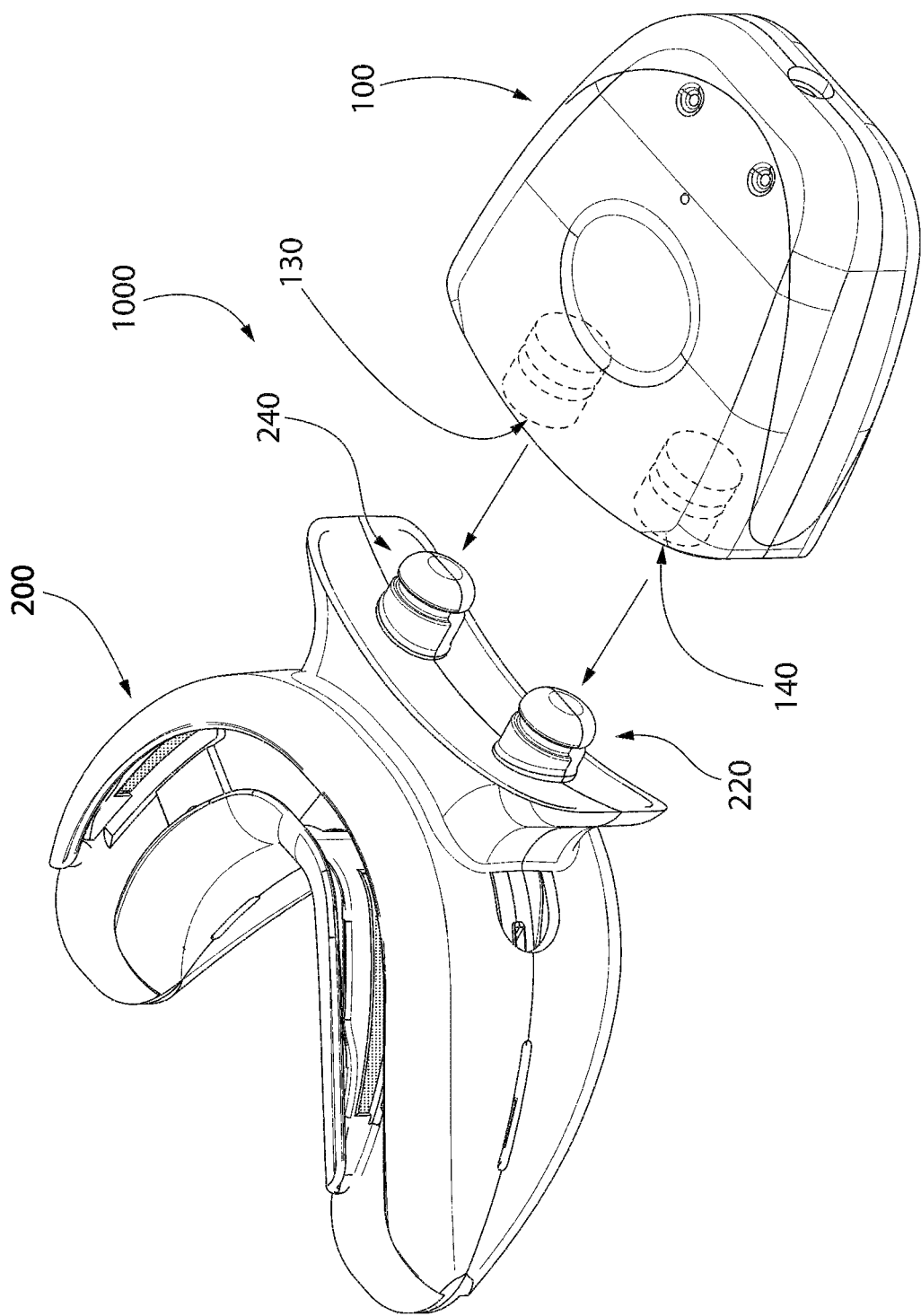
FIG. 5 is a perspective view of the oral cavity treatment device of FIG. 4 wherein the power component has been rotated 180° relative to the tray component.

Referring to FIG. 5, the oral cavity treatment device 1000 is illustrated with the power component 100 having been rotated 180° relative to the tray component 200. In FIG. 5, the bottom surface of the power component 100 is visible whereas in FIGS. 1 and 4 the top surface of the power component 100 was visible, thus indicating that the power component 100 has been rotated. As shown in FIG. 5, the next step in the process is to reattach the power component 100 to the tray component 200 by moving the power and tray components 100, 200 towards one another until the first and second connection members 220, 240 of the tray component 200 engage or mate with the third and fourth connection members 130, 140 (shown with phantom lines) of the power component 100. However, because the power component 100 has been rotated relative to the tray component 200, now the first connection member 220 of the tray component 200 will mate with the fourth connection member 140 of the power component 100 and the second connection member 240 of the tray component 200 will mate with the third connection member 130 of the power component. This change will also cause a reversal of the polarity of the first and second electrodes 210, 211.

Figure 7:
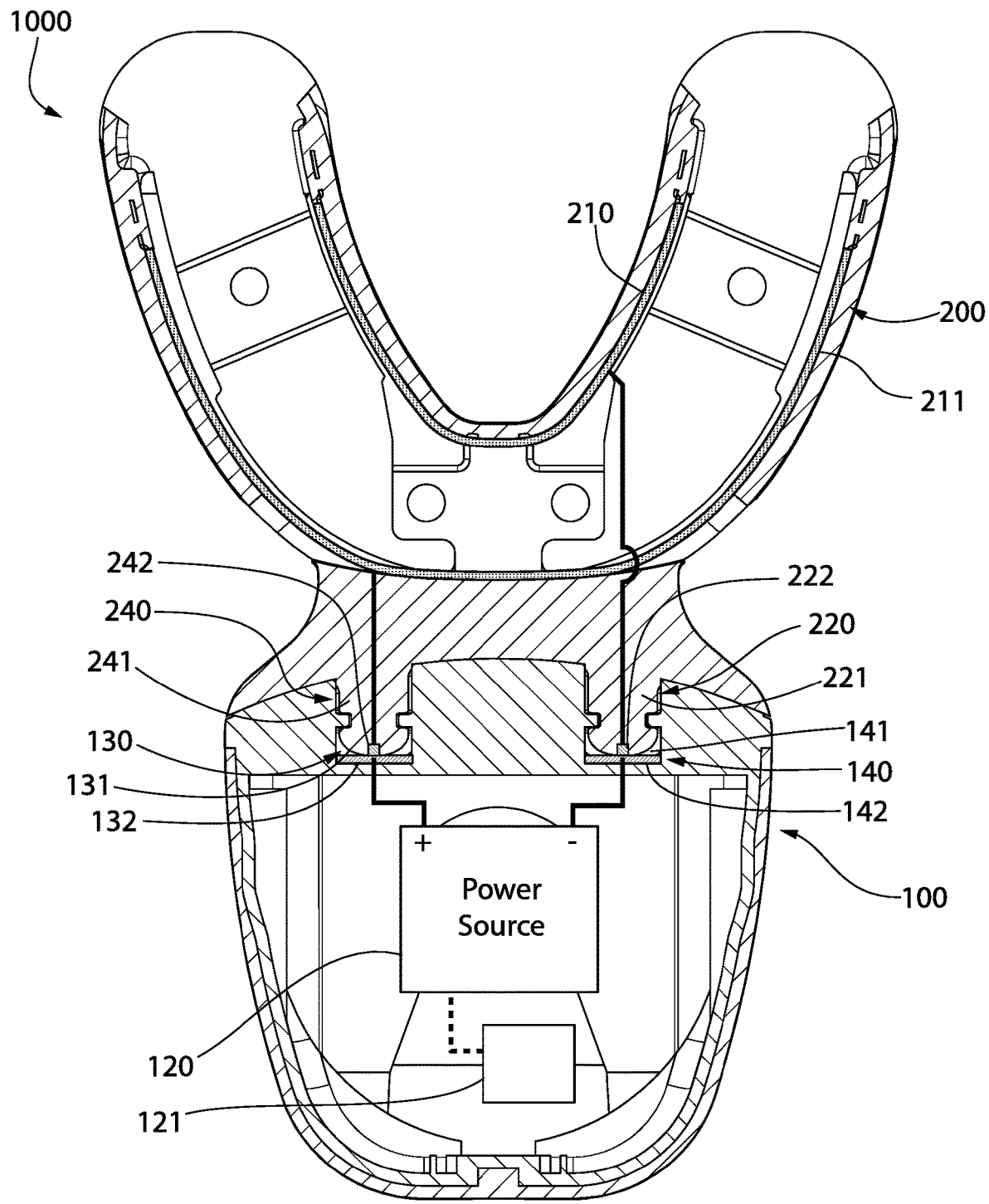
FIG. 7 is a cross-sectional view taken along line VII-VII of FIG. 6.

Referring to FIGS. 6 and 7, the oral cavity treatment device 1000 is illustrated in the second assembled configuration. As noted above, in the second assembled configuration the first connection member 220 of the tray component 200 mates with the fourth connection member 140 of the power component 100 and the second connection member 240 of the tray component 200 will mate with the third connection member 130 of the power component. As a result, the first contact element 222 of the tray component 200 contacts the fourth contact element 142 of the power component 100 to thereby operably couple the first electrode 210 to the negative terminal of the power source 120. Similarly, the second contact element 242 of the tray component 200 contacts the third contact element 132 of the power component 100 to thereby operably couple the second electrode 211 to the positive terminal of the power source 120. Thus, as compared with the first assembled configuration shown in FIGS. 1 and 2, the polarity of the first and second electrodes 210, 211 has been reversed.

Figure 8:
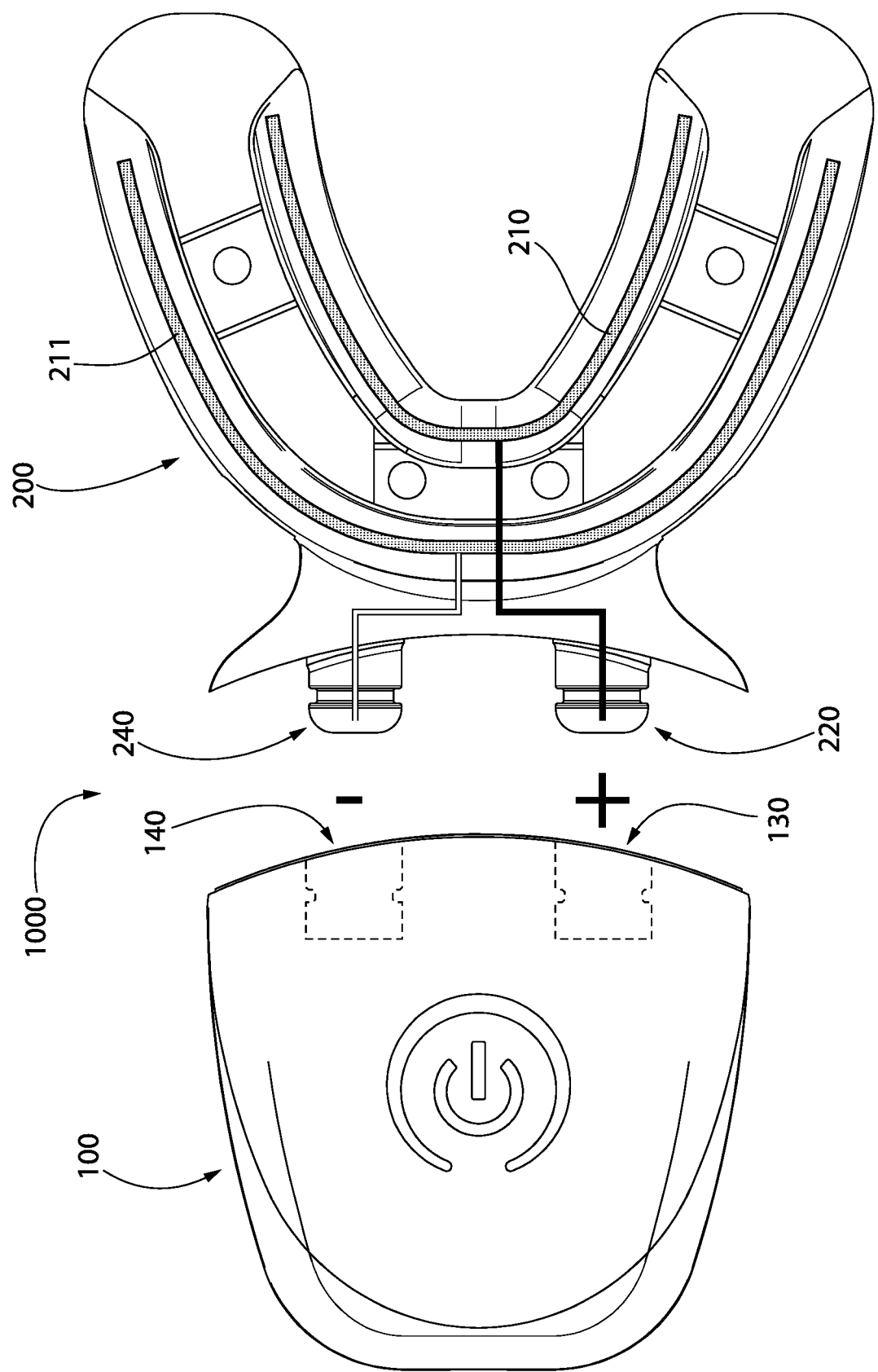
FIG. 8 is a schematic illustration of the oral cavity treatment device of FIG. 1 showing the polarities of electrodes of the tray component when in the first assembled configuration.
Figure 9:
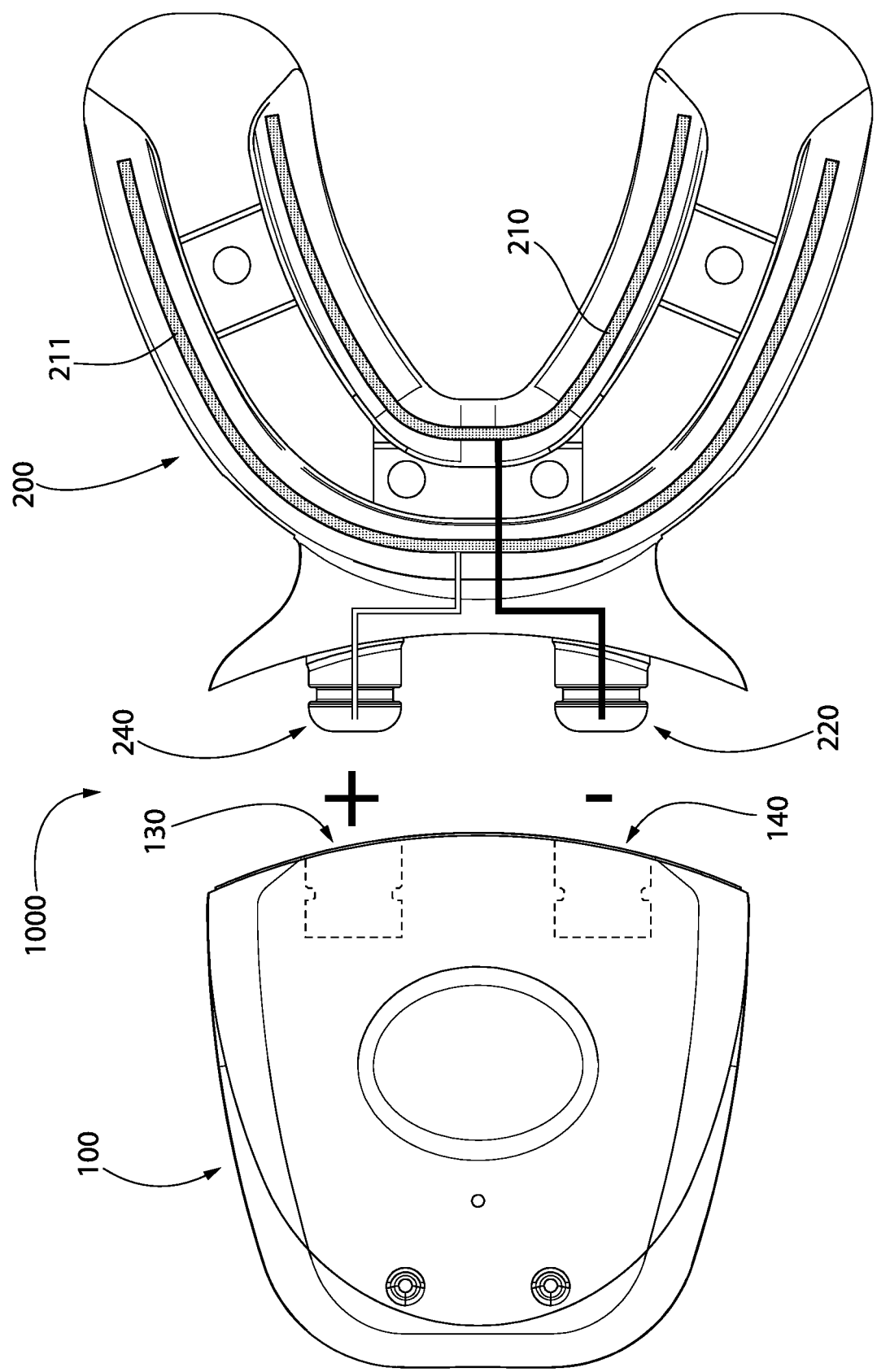
FIG. 9 is a schematic illustration of the oral cavity treatment device of FIG. 1 showing the polarities of the electrodes of the tray component when in the second assembled configuration.

FIGS. 7 and 8 schematically illustrate the tray component 200 and the power component 100 in a detached state, but in preparation to be coupled into one of the first and second attached configurations. Specifically, in FIG. 7, upon the tray component 200 and the power component 100 being attached, the first electrode 210 will be operably coupled to the positive terminal of the power source and the second electrode 211 will be operably coupled to the negative terminal of the power source. In FIG. 8, upon the tray component 200 and the power component 100 being attached, the first electrode 210 will be operably coupled to the negative terminal of the power source and the second electrode 211 will be operably coupled to the positive terminal of the power source. Thus, this again shows that by rotating one of the power component 100 and the tray component 200 relative to the other, the power component 100 and the tray component 200 can be coupled together in two different configurations, which results in reversing the polarities of the first and second electrodes 210, 211.

Figure 10:
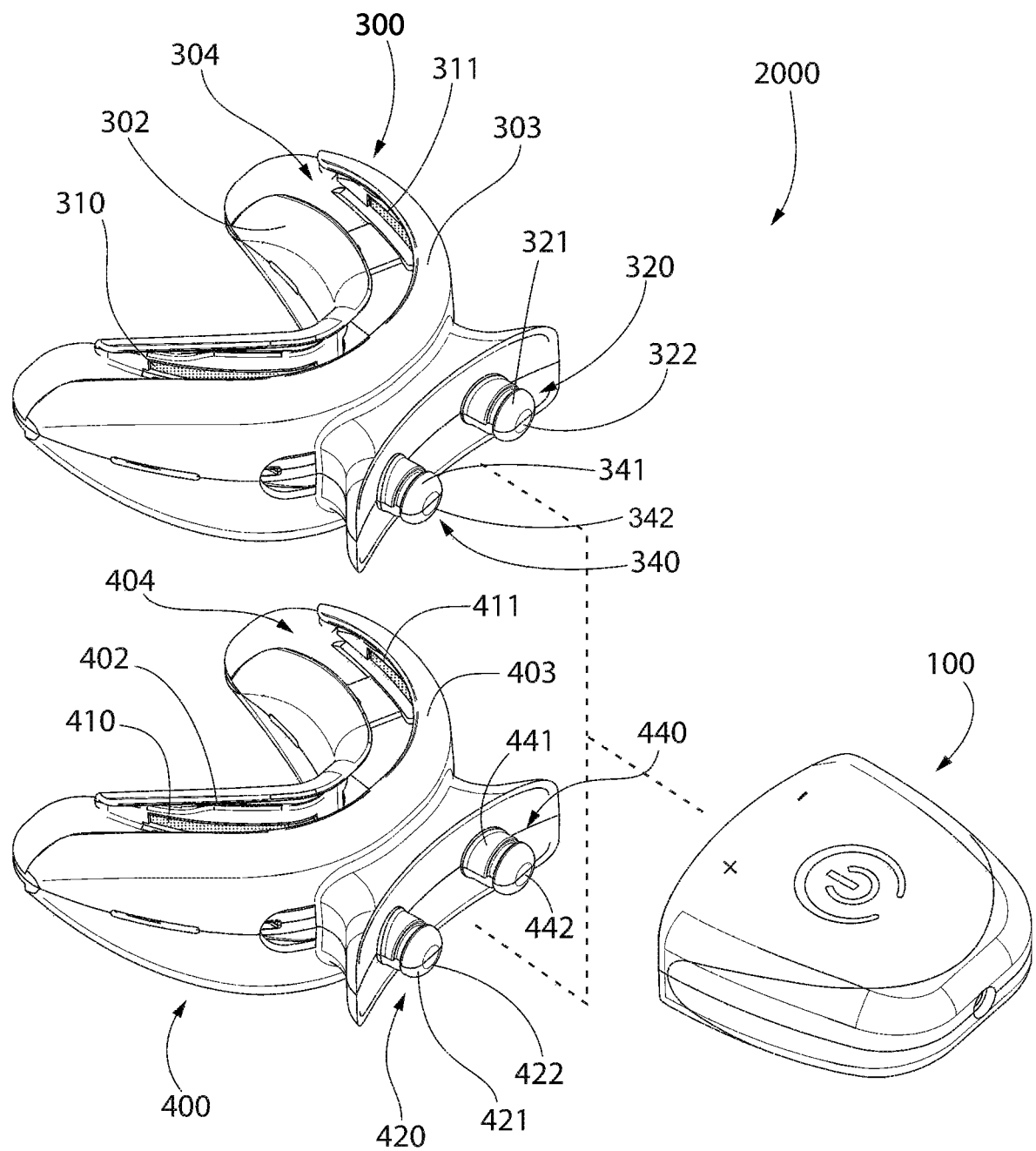
FIG. 10 is a perspective view of an oral cavity treatment kit including a power component and two distinct tray components that are detachable thereto.

Referring now to FIG. 10, an oral cavity treatment kit 2000 is illustrated in accordance with an embodiment of the present invention. The oral cavity treatment kit 2000 generally comprises the power component 100 as described above, a first tray component 300 that is identical to the tray component 200 as described above, and a second tray component 400 that is identical to the tray component 200 as described above. The first and second tray components 300, 400 are structurally identical with the only difference being that they may include electrodes having different materials. The structural details of the power component 100 and of the first and second tray components 300, 400 will not be described herein in the interest of brevity, it being understood that the description of the power component 100 provided above as well as the description of the tray component 200 described above is applicable.

In this embodiment, both the first and second tray components 300, 400 are configured to be coupled to the power component 100 both mechanically/physically and electronically in the exact same manner as has been described above. Thus, mechanically coupling the first or second tray components 300, 400 to the power component 100 also results in operably coupling the electrodes of the first or second tray component 300, 400 to the power source of the power component 100.

The first tray component 300 comprises an inner sidewall 302, an outer sidewall 303, and an upper tooth receiving cavity 304 defined therebetween. Furthermore, the first tray component 300 comprises a first electrode 310 located along the inner sidewall 302 and a second electrode 311 located along the outer sidewall 303, the first and second electrodes 310, 311 being located on opposite sides of the upper teeth receiving channel 304 (and it may also include electrodes on opposite sides of a lower teeth receiving channel as described above).

The second tray component 400 comprises an inner sidewall 402, an outer sidewall 403, and an upper tooth receiving cavity 404 defined therebetween. Furthermore, the second tray component 400 comprises a first electrode 310 located along the inner sidewall 402 and a second electrode 411 located along the outer sidewall 303, the first and second electrodes 410, 411 being located on opposite sides of the upper teeth receiving channel 404 (and it may also include electrodes on opposite sides of a lower teeth receiving channel as described above).

In some embodiments, the first and second electrodes 310, 311 of the first tray component 300 may be formed of a first material and the first and second electrodes 410, 411 of the second tray component 400 may be formed of a second material that is different than the first material. For example, the first material may be titanium and the second material may be zinc. Of course, other materials could be used in other embodiments. Thus, the first and second tray components 300, 400 can both be used with the power component 100 to provide a different treatment to a user, based on the material of the electrodes and a type of oral treatment composition placed in the respective tooth receiving channel during a treatment. Moreover, in still other embodiments the first and second electrodes 310, 311 of the first tray component 300 may be formed of the same material as the first and second electrodes 410, 411 of the second tray component 400 so that the same power component 100 can be used to two tray components 300, 400 that are identical but belong to different users.

The first tray component 300 comprises a first connection member 320 comprising a first mechanical connector 321 and a first electrical contact 322 and a second connection member 340 comprising a second mechanical connector 341 and a second electrical contact 342. The first electrical contact 322 is operably coupled to the first electrode 310 and the second electrical contact 342 is operably coupled to the second electrode 311. The second tray component 400 comprises a first connection member 420 comprising a first mechanical connector 421 and a first electrical contact 422 and a second connection member 440 comprising a second mechanical connector 441 and a second electrical contact 442. The first electrical contact 422 is operably coupled to the second electrode 411 and the second electrical contact 442 is operably coupled to the first electrode 410.

As can be seen, the first tray component 300 is intended to be coupled to the power component 100 so that the first electrical contact 322 is coupled to the negative terminal of the power source and the second electrical contact 342 is coupled to the positive terminal of the power source. Thus, with the first tray component 300, the first electrode 310 is operably coupled to the negative terminal of the power source and the second electrode 311 is operably coupled to the positive terminal of the power source. Of course, this can be reversed in the manner noted above and may be depending on the particular material of the electrodes 310, 311 and the particular treatment being provided.

Moreover, the second tray component 400 is intended to be coupled to the power component 100 so that the first electrical contact 422 is coupled to the positive terminal of the power source and the second electrical contact 442 is coupled to the negative terminal of the power source. Thus, with the second tray component 400, the first electrode 410 is operably coupled to the positive terminal of the power source and the second electrode 411 is operably coupled to the negative terminal of the power source. Of course, this can be reversed in the manner noted above and may be depending on the particular material of the electrodes 410, 411 and the particular treatment being provided.

Thus, it should be appreciated that tray components 300, 400 that are identical to one another except with regard to the material of the electrodes may be used with the same power component 100 to provide different treatments to a user. The tray components 300, 400 can both be coupled to the power component 100 in either configuration described above (i.e., the first attached configuration or the second attached configuration) based on the desired polarity of the electrodes of that tray component.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral cavity treatment device comprising:
a power component comprising a housing having a cavity and a power source located in the cavity;
a tray component comprising a tooth receiving channel, a first electrode operably coupled to a first electrical contact, and a second electrode operably coupled to a second electrical contact, the first and second electrodes being located on opposite sides of the tooth receiving channel; and
wherein the tray component is detachably coupled to the power component in: (1) a first configuration whereby the first electrical contact is operably coupled to a positive terminal of the power source and the second electrical contact is operably coupled to a negative terminal of the power source; and (2) a second configuration whereby the first electrical contact is operably coupled to the negative terminal of the power source and the second electrical contact is operably coupled to the positive terminal of the power source;
wherein the housing of the power component comprises a first engagement surface and the tray component comprises a second engagement surface that mates with the first engagement surface when the tray component is attached to the power component.

2. The oral cavity treatment device according to claim 1 wherein altering the coupling between the tray component and the power component from the first configuration to the second configuration comprises detaching the tray component from the power component and then reattaching the tray component to the power component in a different relative configuration.

3. The oral cavity treatment device according to claim 1 wherein altering the coupling between the tray component and the power component from the first configuration to the second configuration comprises detaching the tray component from the power component, rotating one of the tray component and the power component 180° relative to the other one of the tray component and the power component, and then reattaching the tray component to the power component.

4. The oral cavity treatment device according to claim 1 further comprising a first connection cavity and a second connection cavity formed into the first engagement surface of the housing of the power component, a third electrical contact located within the first connection cavity and operably coupled to the positive terminal of the power source and a fourth electrical contact located within the second connection cavity and operably coupled to the negative terminal of the power source, wherein the first electrical contact of the tray component contacts one of the third and fourth electrical contacts to operably couple the first electrode to one of the positive and negative terminals of the power source, and wherein the second electrical contact of the tray component contacts the other of the third and fourth electrical contacts to operably couple the second electrode to the other one of the positive and negative terminals of the power source.

5. The oral cavity treatment device according to claim 4 further comprising a first protuberance and a second protuberance extending from the second engagement surface of the tray, the first electrical contact being located on the first protuberance and the second electrical contact being located on the second protuberance, and wherein the first protuberance is disposed within one of the first and second connection cavities and the second protuberance is disposed within the other one of the first and second connection cavities to couple the tray component to the power component.

6. The oral cavity treatment device according to claim 1 further comprising:
the tray component comprising:
a first mechanical connector, the first electrical contact being located along the first mechanical connector; and
a second mechanical connector, the second electrical contact being located along the second mechanical connector;
the housing of the power component comprising:
a third mechanical connector, a third electrical contact that is operably coupled to a positive terminal of the power source being located along the third mechanical connector; and
a fourth mechanical connector, a fourth electrical contact that is operably coupled to a negative terminal of the power source being located along the second mechanical connector.

7. The oral cavity treatment device according to claim 6 further comprising:
wherein in the first configuration the first mechanical connector is coupled to the third mechanical connector so that the first electrical contact is in contact with the third electrical contact and the second mechanical connector is coupled to the fourth mechanical connector so that the second electrical contact is in contact with the fourth electrical contact; and
wherein in the second configuration the first mechanical connector is coupled to the fourth mechanical connector so that the first electrical contact is in contact with the fourth electrical contact and the second mechanical connector is coupled to the third mechanical connector so that the second electrical contact is in contact with the third electrical contact.

8. The oral cavity treatment device according to claim 6 wherein the first and second mechanical connectors comprise a protuberance extending from a rear surface of the tray component and wherein the third and fourth mechanical connectors comprise a cavity that is configured to receive one of the protuberances.

9. The oral cavity treatment device according to claim 1 further comprising:
a first protuberance extending from a rear surface of the tray component, the first electrical contact being exposed on a distal end of the first protuberance;
a second protuberance extending from a rear surface of the tray component, the second electrical contact being exposed on a distal end of the second protuberance;
a first connection cavity formed into the housing of the power component, a third electrical contact that is operably coupled to the positive terminal of the power source being located on a floor of the first connection cavity;
a second connection cavity formed into the housing of the power component, a fourth electrical contact that is operably coupled to the negative terminal of the power source being located on a floor of the second connection cavity;
wherein in the first configuration the first protuberance is disposed within the first connection cavity and the first electrical contact is in contact with the third electrical contact and the second protuberance is disposed within the second connection cavity and the second electrical contact is in contact with the fourth electrical contact; and wherein in the second configuration the first protuberance is disposed within the second connection cavity and the first electrical contact is in contact with the fourth electrical contact and the second protuberance is disposed within the first connection cavity and the second electrical contact is in contact with the third electrical contact.

10. An oral cavity treatment device comprising:
a tray component comprising a first electrode and a second electrode located on opposite sides of a tooth receiving channel, a first connection member comprising a first mechanical connector and a first electrical contact that is operably coupled to the first electrode, and a second connection member comprising a second mechanical connector and a second electrical contact that is operably coupled to the second electrode;
a power component comprising a cavity that houses a power source, a third connection member comprising a third mechanical connector and a third electrical contact that is operably coupled to a positive terminal of the power source, and a fourth connection member comprising a third mechanical connector and a fourth electrical contact that is operably coupled to a negative terminal of the power source;
wherein the tray component and the power component are detachably coupled together and can be altered between: (1) a first assembled configuration whereby: (a) the first and third connection members mate so that the first and third mechanical connectors are coupled together and the first and third electrical contacts are in contact to couple the first electrode to the positive terminal of the power source; and (b) the second and fourth connection members mate so that the second and fourth mechanical connectors are coupled together and the second and fourth electrical contacts are in contact to couple the second electrode to the negative terminal of the power source; (2) a second assembled configuration whereby: (a) the first and fourth connection members mate so that the first and fourth mechanical connectors are coupled together and the first and fourth electrical contacts are in contact to couple the first electrode to the negative terminal of the power source; and (b) the second and third connection members mate so that the second and third mechanical connectors are coupled together and the second and third electrical contacts are in contact to couple the second electrode to the positive terminal of the power source; and (3) a disassembled configuration whereby the tray component and the power component are separated from one another.

11. The oral cavity treatment device according to claim 10 wherein the first and second mechanical connectors comprise the same one of a protuberance and a cavity and the third and fourth mechanical connectors comprise the other one of the protuberance and the cavity.

12. The oral cavity treatment device according to claim 11 wherein the first and second mechanical connectors comprise the protuberance, the first and second electrical contacts being exposed along the protuberance, and wherein the third and fourth mechanical connectors comprise the cavity, the third and fourth electrical contacts being recessed relative to an outer surface of the power component within the cavities.

13. The oral cavity treatment device according to claim 10 wherein altering the coupling between the tray component and the power component from the first attached configuration to the second attached configuration comprises detaching the tray component from the power component, rotating one of the tray component and the power component 180° relative to the other one of the tray component and the power component, and then reattaching the tray component to the power component.

14. An oral cavity treatment kit comprising:
a power component comprising a housing having a cavity and a power source located in the cavity, the power source comprising a positive terminal and a negative terminal;
a first tray component comprising a tooth receiving channel defined between inner and outer sidewalls, a first electrode located along the inner sidewall, and a second electrode located along the outer sidewall; and
a second tray component comprising a tooth receiving channel defined between inner and outer sidewalls, a first electrode located along the inner sidewall, and a second electrode located along the outer sidewall;
wherein at least one of:
the first electrode of the first tray component is formed from a different material than the first electrode of the second tray component; and
the second electrode of the first tray component is formed from a different material than the second electrode of the second tray component;
wherein the first tray component is detachably coupled to the power component so that the first electrode is operably coupled to one of the positive and negative terminals of the power source and the second electrode is operably coupled to the other one of the positive and negative terminals of the power source; and
wherein the second tray component is detachably coupled to the power component so that the first electrode is operably coupled to one of the positive and negative terminals of the power source and the second electrode is operably coupled to the other one of the positive and negative terminals of the power source.

15. The oral cavity treatment kit according to claim 14 wherein the first tray component is configured to be coupled to the power component so that the first electrode is operably coupled to the positive terminal of the power source and the second electrode is operably coupled to the negative terminal of the power source, and wherein the second tray component is configured to be coupled to the power component so that the first electrode is operably coupled to the negative terminal of the power source and the second electrode is operably coupled to the positive terminal of the power source.

16. The oral cavity treatment kit according to claim 14 wherein the coupling of each of the first and second tray components to the power component is alterable between: (1) a first configuration whereby the first electrode is operably coupled to the positive terminal of the power source and the second electrode is operably coupled to the negative terminal of the power source; and (2) a second configuration whereby the first electrode is operably coupled to the negative terminal of the power source and the second electrode is operably coupled to the positive terminal of the power source.

17. The oral cavity treatment kit according to claim 14 wherein the first and second tray components comprise protuberances that are received within cavities of the power component when the first and second tray components are coupled to the power component, and wherein the first and second tray components comprise electrical contacts located along the protuberances and the power component comprises electrical contacts located within the cavities that are operably coupled to the positive and negative terminals of the power source, respectively, so that the electrical contacts of the first and second tray components come into contact with the electrical contacts of the power component when the first and second tray components are coupled to the power component to couple the first and second electrodes of the first and second tray components to the power source.

18. The oral cavity treatment kit according to claim 14 wherein mechanically coupling the first tray component to the power component causes the first and second electrodes of the first tray component to become electrically coupled to the power source, and wherein mechanically coupling the second tray component to the power component causes the first and second electrodes of the second tray component to become electrically coupled to the power source.

19. The oral cavity treatment kit according to claim 14 wherein the first and second trays are structurally identical except with regard to the first and second materials of the first and second electrodes.

\* \* \* \* \*